US012544277B2

(12) United States Patent
Murray et al.

(10) Patent No.: US 12,544,277 B2
(45) Date of Patent: Feb. 10, 2026

(54) PROTECTORS OF RECONSTRUCTED NIPPLES IN HUMAN POST-MASTECTOMY BREAST RECONSTRUCTION

(71) Applicant: UNIVERSITY OF FLORIDA RESEARCH FOUNDATION, INCORPORATED, Gainesville, FL (US)

(72) Inventors: John D. Murray, Gainesville, FL (US); Sheri Shelley, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 283 days.

(21) Appl. No.: 18/271,100

(22) PCT Filed: Jan. 7, 2022

(86) PCT No.: PCT/US2022/011607
§ 371 (c)(1),
(2) Date: Jul. 6, 2023

(87) PCT Pub. No.: WO2022/150583
PCT Pub. Date: Jul. 14, 2022

(65) Prior Publication Data

US 2024/0074915 A1 Mar. 7, 2024

Related U.S. Application Data

(60) Provisional application No. 63/134,687, filed on Jan. 7, 2021.

(51) Int. Cl.
*A61F 13/14* (2006.01)
*A61F 13/00* (2024.01)

(52) U.S. Cl.
CPC .. *A61F 13/145* (2013.01); *A61F 2013/00574* (2013.01); *A61F 2013/00859* (2013.01)

(58) Field of Classification Search
CPC .......... A61F 13/145; A61F 2013/00574; A61F 2013/00859; A61F 13/14; A61F 13/143;
(Continued)

(56) References Cited

U.S. PATENT DOCUMENTS

| | | | | |
|---|---|---|---|---|
| 5,743,272 A * | 4/1998 | Kocher, Jr. | ............. | A61J 13/00 128/890 |
| 6,241,715 B1 * | 6/2001 | Houser | ................. | A61F 13/141 604/385.07 |

(Continued)

FOREIGN PATENT DOCUMENTS

| | | | |
|---|---|---|---|
| EP | 3054913 B1 * | 3/2018 | .............. A61J 13/00 |

OTHER PUBLICATIONS

PCT search report & written opinion, PCT/US2022/011607, mailed Apr. 11, 2022, 10 pages.

(Continued)

*Primary Examiner* — Tarla R Patel
(74) *Attorney, Agent, or Firm* — Timothy H. Van Dyke; Wolter Van Dyke Davis, PLLC

(57) ABSTRACT

Disclosed herein are devices and methods for protecting reconstructed nipples, typically post-surgery. The nipple protector may include a circular base portion and an annular ridge concentrically disposed to define a central aperture. The nipple protector In may further include an adhesive layer disposed on a bottom surface of the base portion for adhering the nipple protector to an area surrounding the reconstructed nipple. The nipple protector is fashioned to allow for direct access to the new nipple, which facilitates application of antibiotic ointments. The nipple protector
(Continued)

softly adheres to the skin to provide flexible, adherent, comfortable, and water tolerant usage.

19 Claims, 4 Drawing Sheets

(58) Field of Classification Search
CPC .. A61F 13/141; A61F 5/03; A61F 2007/0019; A61F 2007/0021; A61F 2013/15016
See application file for complete search history.

(56) References Cited

U.S. PATENT DOCUMENTS

| | | | | |
|---|---|---|---|---|
| 8,686,214 | B2 | 4/2014 | Hyde-Edwards et al. | |
| 10,271,996 | B2 * | 4/2019 | Hufnagel | A61F 13/145 |
| 2003/0014108 | A1 * | 1/2003 | Lauren | A61F 2/52 623/7 |
| 2005/0239369 | A1 * | 10/2005 | Clark | A61F 13/141 450/81 |
| 2008/0188787 | A1 | 8/2008 | Clark | |
| 2009/0308405 | A1 * | 12/2009 | Yamashita | A61J 13/00 128/890 |
| 2014/0305446 | A1 * | 10/2014 | Raniere | A61F 13/14 128/890 |
| 2016/0262946 | A1 * | 9/2016 | Dickson | A61J 13/00 |
| 2017/0165049 | A1 * | 6/2017 | Horne | A61B 17/00 |

OTHER PUBLICATIONS

Staruch, Robert M.T. et al., "The ideal nipple reconstruction sheild", PRS Journal, 2019, vol. 143, No. 3, pp. 698-699.

Weissman, Oren et al., "Silicone Nipple Shields: An Innovative Postoperative Dressing Technique After Nipple Reconstruction", Aesth Plast Surg., 2010, vol. 34, pp. 48-51.

* cited by examiner

PROTECTORS OF RECONSTRUCTED NIPPLES IN HUMAN POST-MASTECTOMY BREAST RECONSTRUCTION

CROSS-REFERENCE TO RELATED APPLICATION

This application claims the benefit of U.S. Provisional Patent Application No. 63/134,687, filed Jan. 7, 2021, titled PROTECTORS OF RECONSTRUCTED NIPPLES IN HUMAN POST-MASTECTOMY BREAST RECONSTRUCTION, which is incorporated by reference herein in its entirety.

BACKGROUND

In 2016, almost 110,000 breast reconstructions were performed in the US. While a preference of the individual, nipple reconstruction is an option after nipple-sacrificing skin sparing mastectomy. Currently, one of the most common methods of nipple reconstruction uses local skin flaps of the mastectomy to reconstruct the new nipple(s). As skin does not have smooth muscle, unlike the native nipple, nipple projection is sacrificed due to external pressure (from clothing) and natural scar formation over the first 4-6 weeks postoperatively.

Therefore, a need exists to protect the reconstructed nipple at least for the crucial first 4-6 weeks. Doing so would help to preserve projection and naturally protect the flaps from potential injurious pressure. Currently, no protector exists, which allows for direct access to the new nipple. Access to the new nipple allows for the application of antibiotic ointments. Additionally, no existing protectors softly adhere to the skin to provide flexible, adherent, comfortable, water tolerant usage.

The discussion of shortcomings and needs existing in the field prior to the present invention is in no way an admission that such shortcomings and needs were recognized by those skilled in the art prior to the present disclosure.

BRIEF SUMMARY

Various embodiments relate to a nipple protector for protecting a reconstructed nipple. The nipple protector may include a circular base portion and an annular ridge concentrically disposed to define a central aperture. The nipple protector may further include an adhesive layer disposed on a bottom surface of the base portion for adhering the nipple protector to an area surrounding the reconstructed nipple. The circular base portion may have a diameter of about 46 mm, and a thickness of about 1 mm. The annular ridge may have an outer diameter of from about 15 to about 17 mm, an inner diameter of from about 12 to about 14 mm; and a thickness of about 4 to about 5 mm, inclusive of the thickness of the circular base portion.

According to various embodiments, the circular base portion may have tapered sidewalls. According to various embodiments, the circular base portion may have rounded sidewalls. According to various embodiments, the nipple protector may include, comprise, consist of, or be made of one or more elastomeric polymers. According to various embodiments, the elastomeric polymer may be a silicone polymer. According to various embodiments, at least the circular base portion may include or be covered with a nonwoven fabric material.

Various embodiments relate to a method for treating a reconstructed nipple. The method according to various embodiments may include applying a nipple protector as described in any of the various embodiments described herein to the reconstructed nipple. The method for treating a reconstructed nipple may include applying a nipple protector to a reconstructed nipple. The applying may include aligning the central aperture with the reconstructed nipple. Additionally or alternatively, the applying may include contacting the adhesive layer to an area surrounding the reconstructed nipple. According to various embodiments, the method may further include accessing the reconstructed nipple through the central aperture. Accessing the reconstructed nipple through the central aperture may include applying an antibiotic ointment or medicament. According to various embodiments, the method may further include leaving the applied nipple protector in place on the reconstructed nipple for a period of from 4 to 6 weeks. According to various embodiments, the method may further include washing the area surrounding the reconstructed nipple as well as the nipple protector with water. The adhesive layer may tolerate the washing and the nipple protector may remain in place as positioned or adhered to the area surrounding the reconstructed nipple.

These and other features, aspects, and advantages of various embodiments will become better understood with reference to the following description, figures, and claims.

BRIEF DESCRIPTION OF THE FIGURES

Many aspects of this disclosure can be better understood with reference to the following figures.

Figure 1:
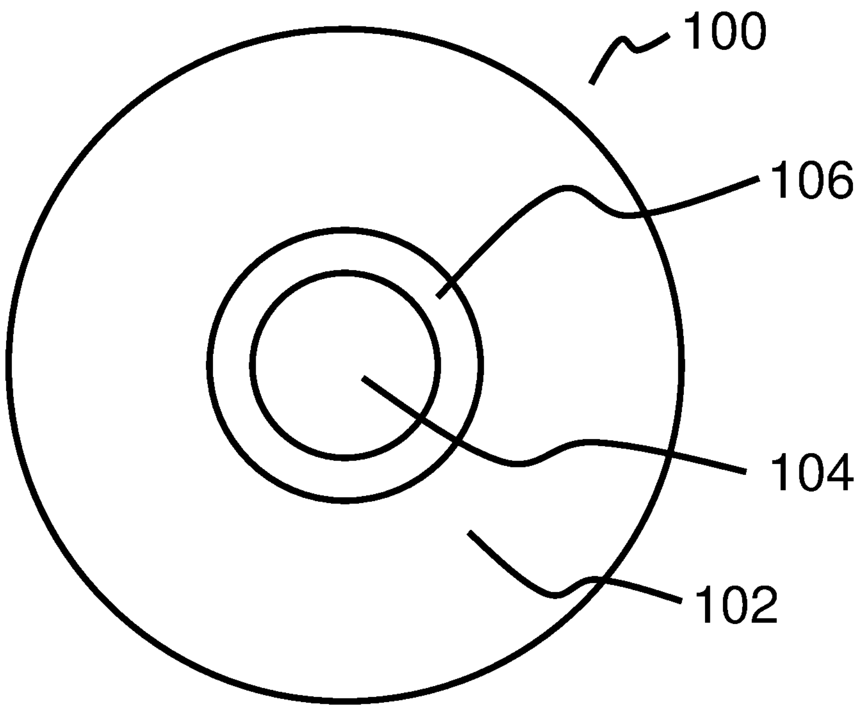
FIG. 1 is an example according to various embodiments, illustrating a top view of a nipple protector.

It should be understood that the various embodiments are not limited to the examples illustrated in the figures.

DETAILED DESCRIPTION

Introduction and Definitions

This disclosure is written to describe the invention to a person having ordinary skill in the art, who will understand that this disclosure is not limited to the specific examples or embodiments described. The examples and embodiments are single instances of the invention which will make a much larger scope apparent to the person having ordinary skill in the art. Unless defined otherwise, all technical and scientific terms used herein have the same meaning as commonly understood by the person having ordinary skill in the art. It is also to be understood that the terminology used herein is for the purpose of describing examples and embodiments only, and is not intended to be limiting, since the scope of the present disclosure will be limited only by the appended claims.

All the features disclosed in this specification (including any accompanying claims, abstract, and drawings) may be replaced by alternative features serving the same, equivalent, or similar purpose, unless expressly stated otherwise. Thus, unless expressly stated otherwise, each feature disclosed is one example only of a generic series of equivalent or similar features. The examples and embodiments described herein are for illustrative purposes only and that various modifications or changes in light thereof will be suggested to the person having ordinary skill in the art and are to be included within the spirit and purview of this application. Many variations and modifications may be made to the embodiments of the disclosure without departing substantially from the spirit and principles of the disclosure. All such modifications and variations are intended to be included herein within the scope of this disclosure. For example, unless otherwise indicated, the present disclosure is not limited to particular materials, reagents, reaction materials, manufacturing processes, or the like, as such can vary. It is also to be understood that the terminology used herein is for purposes of describing particular embodiments only and is not intended to be limiting. It is also possible in the present disclosure that steps can be executed in different sequence where this is logically possible.

All numeric values are herein assumed to be modified by the term "about," whether or not explicitly indicated. The term "about" generally refers to a range of numbers that one of skill in the art would consider equivalent to the recited value (for example, having the same function or result). In many instances, the term "about" may include numbers that are rounded to the nearest significant figure.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by prior disclosure. Further, the dates of publication provided could be different from the actual publication dates that may need to be independently confirmed.

General Discussion

FIG. 1 is an example according to various embodiments, illustrating a top view of a nipple protector 100. The nipple protector 100 may include a circular base portion 102 and an annular ridge 106 that together define a central aperture 104.

Figure 2:
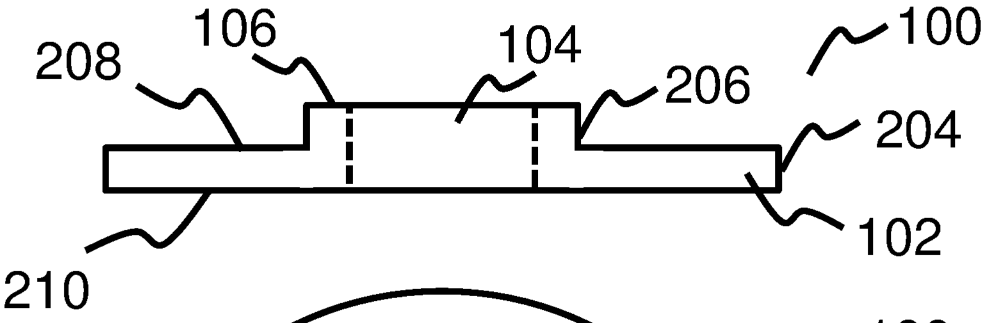
FIG. 2 is an example according to various embodiments, illustrating a side view of a nipple protector.
Figure 4:
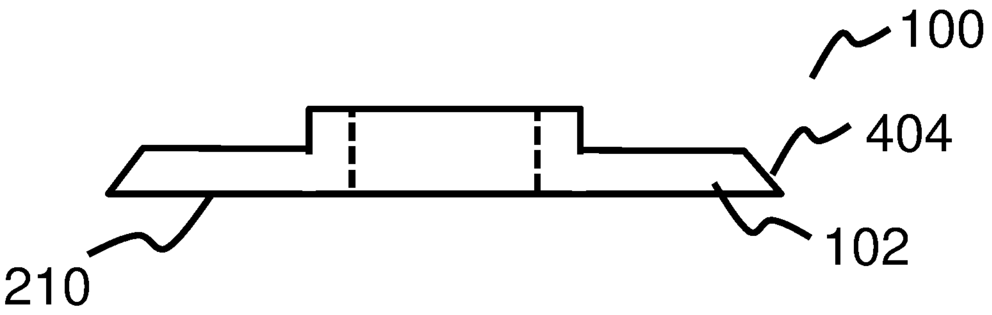
FIG. 4 is an example according to various embodiments, illustrating a side view of a nipple protector.
Figure 5:
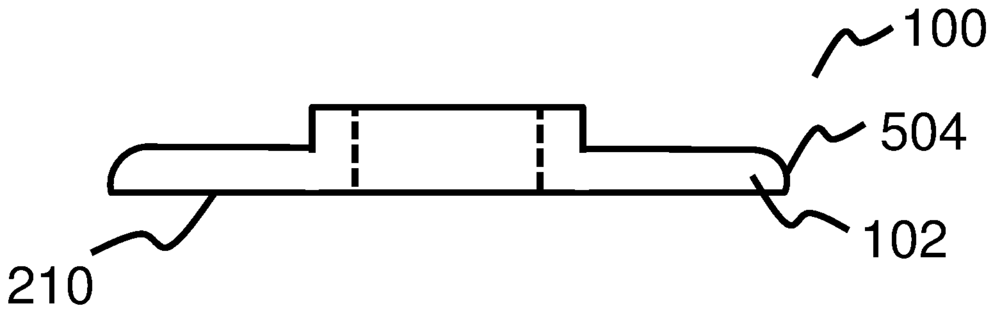
FIG. 5 is an example according to various embodiments, illustrating a side view of a nipple protector.

FIG. 2 is an example according to various embodiments, illustrating a side view of nipple protector 100. The circular base portion 102 may be defined by base sidewalls 204, which may have any suitable shape, including but not limited to flat, tapered, curved, or rounded. FIG. 4 is an example according to various embodiments, illustrating a side view of a nipple protector 100 having tapered base sidewalls 404. FIG. 5 is an example according to various embodiments, illustrating a side view of a nipple protector having rounded base sidewalls 504. The annular ridge 106 may have ridge sidewalls 206, extending above a top surface 208 of the circular base portion 102. The circular base portion 102 may also have a bottom surface 210.

Figure 3:
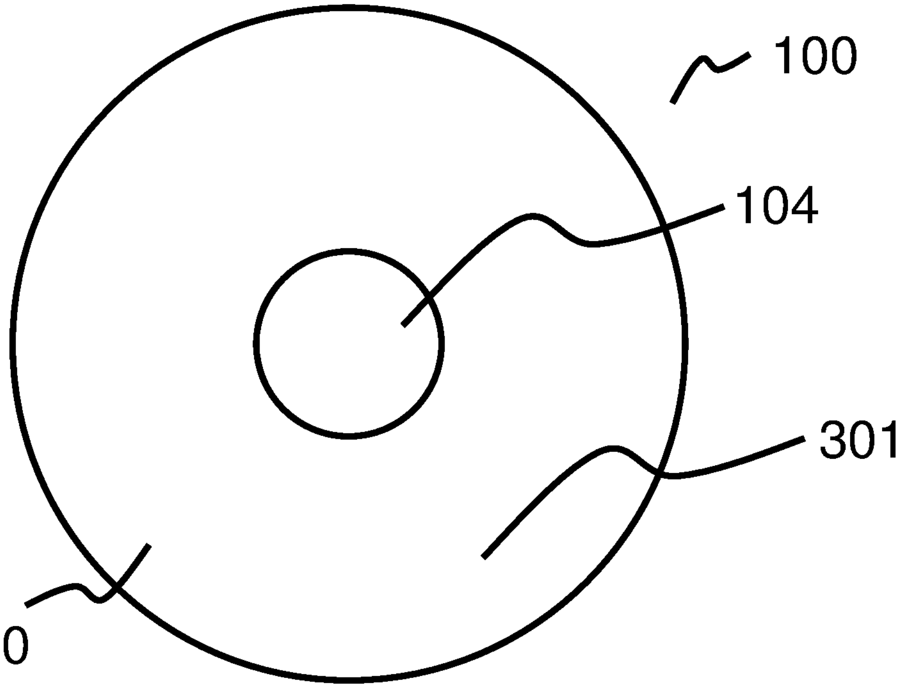
FIG. 3 is an example according to various embodiments, illustrating a bottom view of a nipple protector.

FIG. 3 is an example according to various embodiments, illustrating a bottom view of nipple protector 100. The bottom surface 210 of the nipple protector 100 may include an adhesive layer 301 over all or a portion thereof.

Materials of Construction

The nipple protector 100 may be constructed from any suitable material or combination of materials. The suitable materials should allow the nipple protector 100 to be flexible yet protective. For example, the circular base portion 102 may be flexible and pliable and the annular ridge 106 may be more rigid to provide protection.

According to various embodiments, the entire nipple protector 100 may be formed from an elastomeric polymer, including but not limited to a medical-grade silicone polymer. According to other embodiments the annular ridge 106 may include an elastomeric polymer while the circular base portion 102 may be made at least partially from a nonwoven fabric. The nonwoven fabric may be affixed to the annular ridge 106 by an adhesive, for example.

The adhesive layer 301 may comprise be any suitable adhesive, including for example a medical-grade adhesive commonly used in bandages. According to various embodiments, the adhesive may be a single-use adhesive.

Dimensions

The dimensions of the nipple protector 100 according to various embodiments may be readily adjusted by a person having ordinary skill in the art for generalized usage on an as needed basis. For a nipple protector 100 specifically designed and sized for protecting reconstructed nipples, the following dimensions may be useful.

Figure 6:
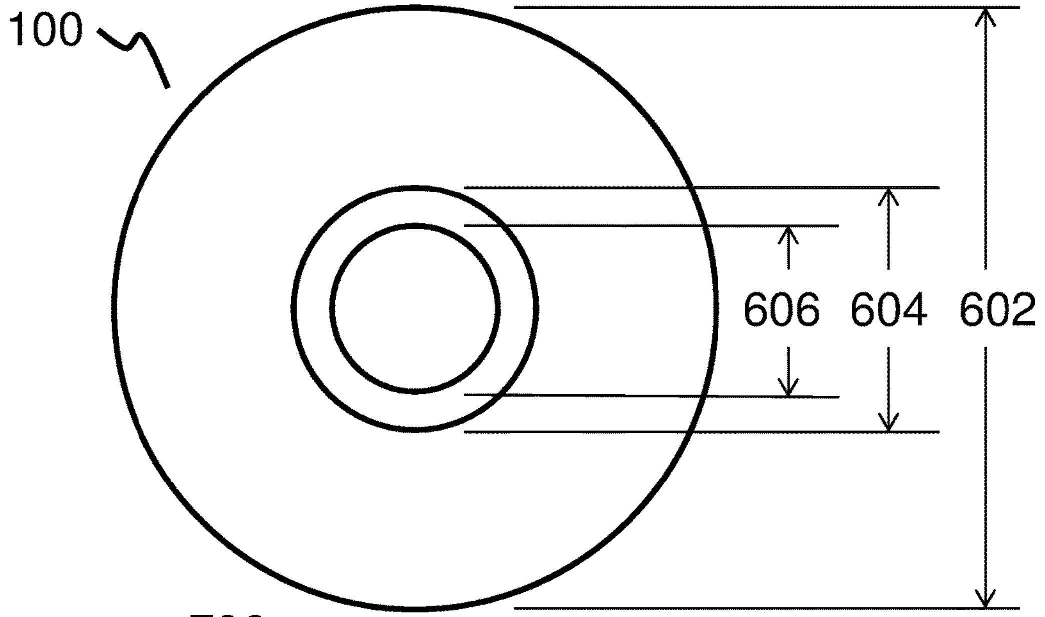
FIG. 6 is an example according to various embodiments, illustrating a top view of a nipple protector.
Figure 8:
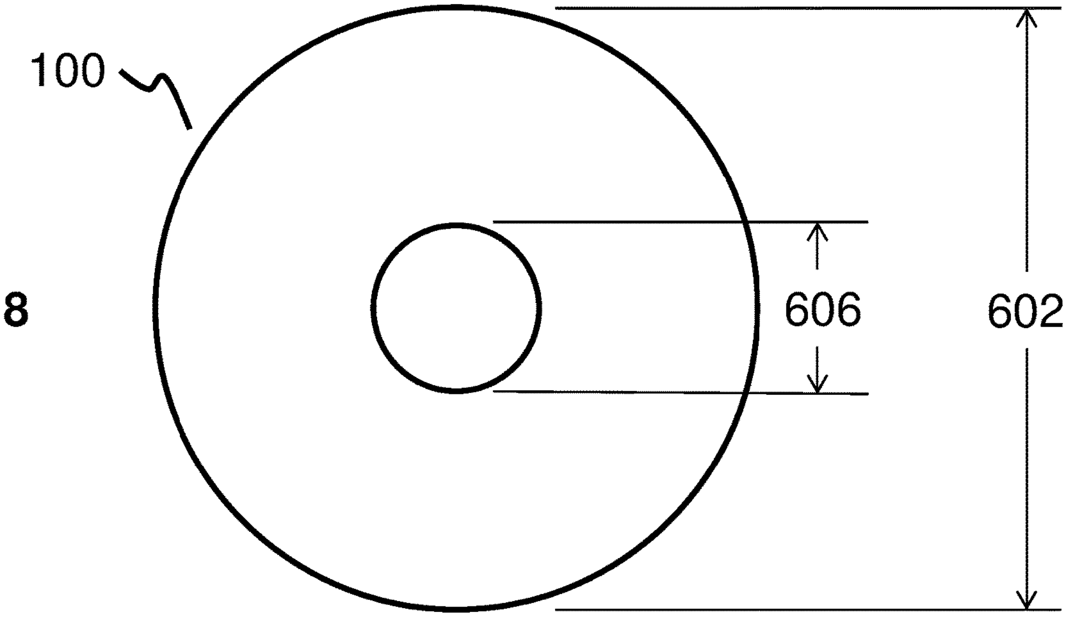
FIG. 8 is an example according to various embodiments, illustrating a bottom view of a nipple protector.

FIG. 6 is an example according to various embodiments, illustrating a top view of a nipple protector 100, showing dimensions that may be particularly suitable for protecting a reconstructed nipple. The circular base portion 102 of the nipple protector 100 may have a diameter 602 of about 46 mm. Diameter 602 is also illustrated in FIG. 8. The annular ridge 106 may have an outer diameter 604 of from about 15 to about 17 mm. The annular ridge 106 may have an inner diameter 606, corresponding to the diameter of the central aperture 104, of from about 12 to about 14 mm. Inner diameter 606 of the central aperture 104 is also illustrated in FIG. 8.

Figure 7:
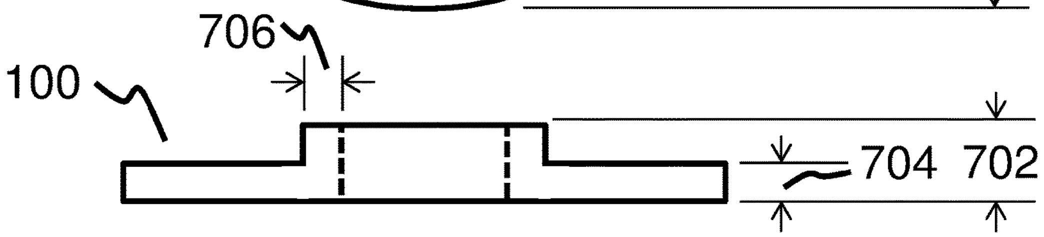
FIG. 7 is an example according to various embodiments, illustrating a side view of a nipple protector.

FIG. 7 is an example according to various embodiments, illustrating a side view of a nipple protector 100, showing dimensions that may be particularly suitable for protecting a reconstructed nipple. The ridge thickness 702 of the nipple protector 100 as measured from the bottom surface 210 of the circular base portion 102 to the top of the annular ridge 106 may be from about 4 to about 5 mm. The base thickness 704 of the circular base portion 102 as measured from the bottom surface 210 to the top surface 208 may be about 1 mm. As can be calculated from the dimensions provided in FIG. 6, the annulus 706 of the annular ridge 106 may be from about 1 to about 5 mm, and is preferably about 3 mm.

Method for Treating a Reconstructed Nipple

Figure 9:
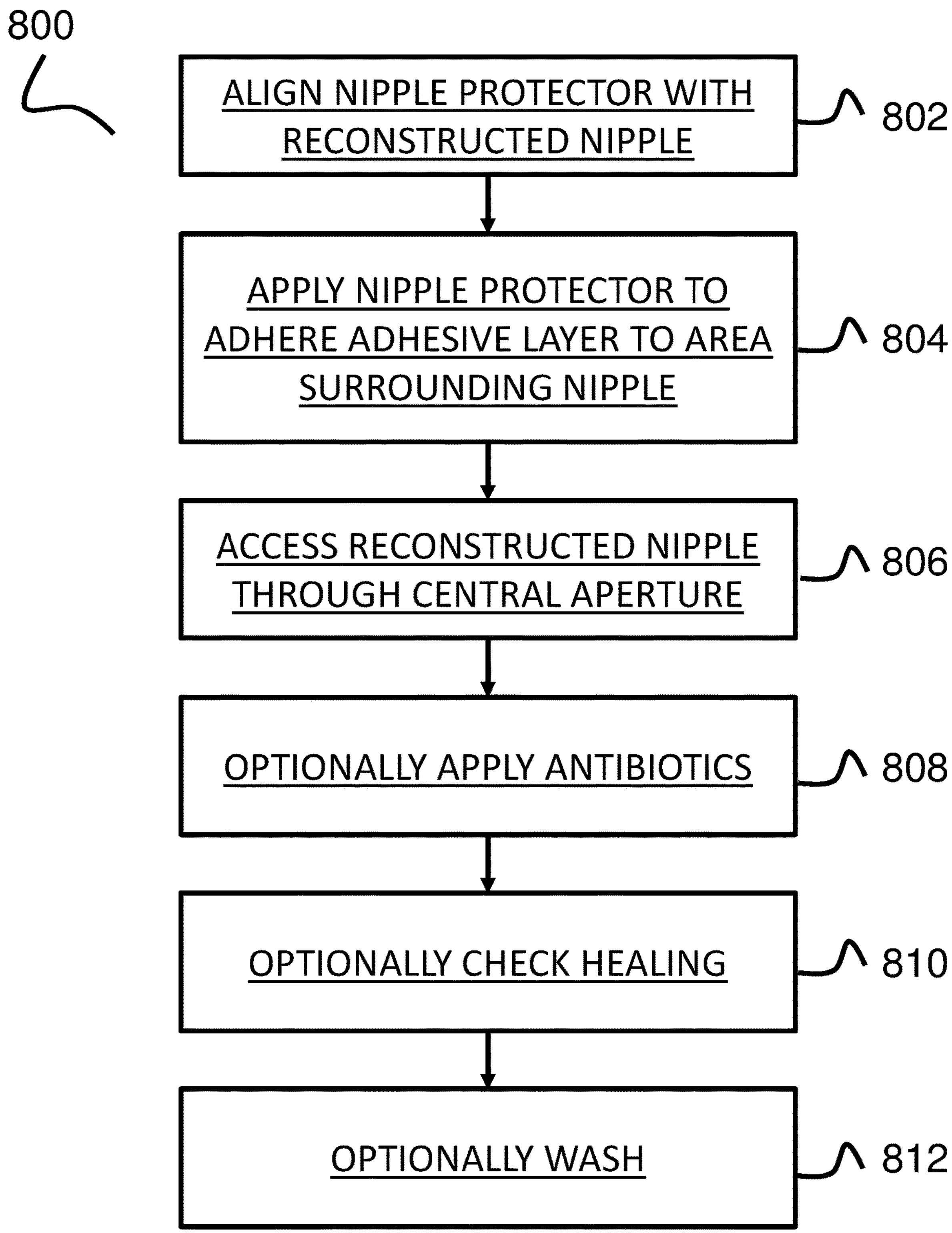
FIG. 9 is an example according to various embodiments, illustrating a schematic diagram of a method of treating a reconstructed nipple.

FIG. 9 is an example according to various embodiments, illustrating a schematic diagram of a method 800 of treating a reconstructed nipple. The method 800 for treating a reconstructed nipple may include applying a nipple protector as described in any of the various embodiments described herein to the reconstructed nipple. For example, the nipple protector may comprise a circular base portion and an annular ridge concentrically disposed to define a central aperture, the nipple protector further comprising an adhesive layer disposed on a bottom surface of the base portion. The circular base portion having a diameter of about 46 mm, and a thickness of about 1 mm. The annular ridge having an outer diameter of from about 15 to about 17 mm, an inner diameter of from about 12 to about 14 mm; and a thickness of about 4 to about 5 mm, inclusive of the thickness of the circular base portion.

The method for treating a reconstructed nipple may include applying a nipple protector to a reconstructed nipple. The applying may include a step 802 of aligning the central aperture with the reconstructed nipple. Additionally or alternatively, the applying may include a step 804 of adhering and/or contacting the adhesive layer to an area surrounding the reconstructed nipple. According to various embodiments, the method may further include a step 806 of accessing the reconstructed nipple through the central aperture. Accessing the reconstructed nipple through the central aperture may include an optional step 808 of applying an antibiotic ointment or medicament. According to various embodiments, the method may further include leaving the applied nipple protector in place on the reconstructed nipple for a period of from 4 to 6 weeks. The method may optionally include a step 810 of checking the progress of healing of the reconstructed nipple. According to various embodiments, the method may further include a step 812 of washing the area surrounding the reconstructed nipple as well as the nipple protector with water. The adhesive layer may tolerate the washing and the nipple protector may remain in place as positioned or adhered to the area surrounding the reconstructed nipple.

What is claimed is:

1. A nipple protector for protecting a reconstructed nipple, the nipple protector comprising a circular base portion and an annular ridge concentrically disposed to define a central aperture that extends from an upper surface of the annular ridge to a bottom surface of the circular base portion, the nipple protector further comprising an adhesive layer disposed on a bottom surface of the base portion,
   - the circular base portion having a diameter of about 46 mm, and a thickness of about 1 mm;
   - the annular ridge having an outer diameter of from about 15 to about 17 mm, an inner diameter of from about 12 to about 14 mm; and a thickness of about 4 to about 5 mm, inclusive of the thickness of the circular base portion,
   - wherein a magnitude of an inner diameter of the central aperture is constant from the upper surface of the annular ridge to the bottom surface of the circular base portion.

2. The nipple protector according to claim 1, wherein the circular base portion has tapered sidewalls.

3. The nipple protector according to claim 1, wherein the circular base portion has rounded sidewalls.

4. The nipple protector according to claim 1, wherein the nipple protector comprises an elastomeric polymer.

5. The nipple protector according to claim 4, wherein the elastomeric polymer is a silicone polymer.

6. The nipple protector according to claim 1, wherein at least the circular base portion comprises a nonwoven fabric material.

7. The nipple protector according to claim 1, wherein the circular base portion and the annular ridge are integral parts of a single body.

8. A method for treating a reconstructed nipple, the method comprising applying a nipple protector to the reconstructed nipple, the nipple protector comprising a circular base portion and an annular ridge concentrically disposed to define a central aperture that extends from an upper surface of the annular ridge to a bottom surface of the circular base portion, the nipple protector further comprising an adhesive layer disposed on a bottom surface of the base portion,
   - the circular base portion having a diameter of about 46 mm, and a thickness of about 1 mm;
   - the annular ridge having an outer diameter of from about 15 to about 17 mm, an inner diameter of from about 12 to about 14 mm; and a thickness of about 4 to about 5 mm, inclusive of the thickness of the circular base portions,
   - wherein a magnitude of an inner diameter of the central aperture is constant from the upper surface of the annular ridge to the bottom surface of the circular base portion.

9. The method according to claim 8, wherein the applying comprises aligning the central aperture with the reconstructed nipple.

10. The method according to claim 8, wherein the applying comprises contacting the adhesive layer to an area surrounding the reconstructed nipple.

11. The method according to claim 8, wherein the circular base portion has tapered sidewalls.

12. The method according to claim 8, wherein the circular base portion has rounded sidewalls.

13. The method according to claim 8, wherein the nipple protector comprises an elastomeric polymer.

14. The method according to claim 8, wherein at least the circular base portion comprises a nonwoven fabric material.

15. The method according to claim 8, the method further comprising accessing the reconstructed nipple through the central aperture.

16. The method according to claim 15, wherein accessing the reconstructed nipple through the central aperture comprises applying an antibiotic ointment or medicament.

17. The method according to claim 8, wherein the method further comprises leaving the applied nipple protector in place on the reconstructed nipple for a period of from 4 to 6 weeks.

18. The method according to claim 8, further comprising washing an area surrounding the reconstructed nipple as well as the nipple protector with water.

19. The method according to claim 18, wherein the adhesive layer tolerates the washing and the nipple protector remains in place as positioned during the applying step.

* * * * *